United States Patent [19]  
Bernath et al.

[11] Patent Number: 4,668,688  
[45] Date of Patent: May 26, 1987

[54] N-SUBSTITUTED ISOQUINOLINE DERIVATIVES AND PHARMACEUTICAL COMPOSITIONS CONTAINING THEM

[75] Inventors: Gabor Bernath; Jeno Kobor; Ferenc Fulop, all of Szeged; Pal Perjesi, Pecs; Elemer Ezer, Budapest; Gyorgy Hajos, Budapest; Eva Palosi, Budapest; Laszlo Denes, Budapest; Laszlo Szporny, Budapest, all of Hungary

[73] Assignee: Richter Gedeon Vegyeszeti Gyar R.T., Budapest, Hungary

[21] Appl. No.: 664,770

[22] Filed: Oct. 25, 1984

[30] Foreign Application Priority Data

Oct. 25, 1983 [HU] Hungary .................. 3652/83

[51] Int. Cl.$^4$ .................. A61K 31/47; C07D 217/16
[52] U.S. Cl. .................. 514/307; 546/146; 546/147; 546/149; 546/150
[58] Field of Search .................. 546/146–147, 546/149–150; 514/307

[56] References Cited

U.S. PATENT DOCUMENTS 3,562,280  2/1971  Leimgruber et al. .............. 546/146  
4,373,104  2/1983  Takács et al. .................. 546/147

OTHER PUBLICATIONS

Chem. Ber. 102, 915 (1969).  
Swinyard et al.: J. Pharmacol. Exp. Ther. 106, 319 (1952).  
Nimegeers C. J. E. et al.: Arzneimittel Forsch. 25:15/9 (1975).

Primary Examiner—Glennon H. Hollrah  
Assistant Examiner—James H. Turnipseed  
Attorney, Agent, or Firm—Keil & Weinkauf

[57] ABSTRACT

The invention relates to new N-substituted bis(hydroxymethyl)-methyl-isoquinoline derivatives of the formula (I), (I)

wherein  
$R^1$ and $R^2$ represent hydroxyl or alkoxy having from 1 to 6 carbon atoms,  
the dotted line is an optional double bond in the 1,2-position,  
$R^3$ is alkyl having from 1 to 6 carbon atoms or aralkyl containing from 1 to 4 carbon atoms in the alkyl moiety, or—if there is a single bond in the 1,2-position—represents a group of the formula $$-\underset{X}{\underset{\|}{C}}-R^4 \text{ or } -\underset{R^5}{\underset{|}{CH}}-\underset{R^6}{\underset{|}{CH}}-OH$$

in which  
X is oxygen if  
$R^4$ is alkyl having from 1 to 5 carbon atoms, alkoxy having from 1 to 4 carbon atoms, hydroxyl, phenyl or substituted phenyl; or  
X is oxygen or sulfur if  
$R^4$ is an $-NH_2$, $-NH-C_{1-4}$-alkyl, $-NH-C_{3-6}$-cycloalkyl, $-NH$-phenyl or $-NH-C_{1-4}$-alkyl-phenyl group; and  
$R^5$ and $R^6$ independently stand for hydrogen, alkyl having from 1 to 4 carbon atoms or phenyl, with the proviso that at least one of them is other than phenyl, and salts thereof. Processes for the preparation of these compounds and pharmaceutical compositions are also within the scope of the invention.

5 Claims, No Drawings

N-SUBSTITUTED ISOQUINOLINE DERIVATIVES AND PHARMACEUTICAL COMPOSITIONS CONTAINING THEM

The invention relates to new N-substituted isoquinoline derivatives. More particularly, the invention concerns new N-substituted bis(hydroxymethyl)-methyl-isoquinoline derivatives of the formula (I),

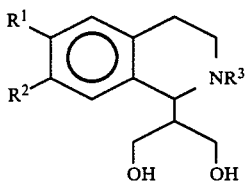
(I)

wherein
$R^1$ and $R^2$ represent hydroxyl or alkoxy having from 1 to 6 carbon atoms,
the dotted line is an optional double bond in the 1,2-position,
$R^3$ is alkyl having from 1 to 6 carbon atoms or aralkyl containing from 1 to 4 carbon atoms in the alkyl moiety, or—if there is a single bond in the 1,2-position—represents a group of the formula

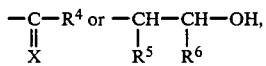

in which
X is oxygen if
$R^4$ is alkyl having from 1 to 5 carbon atoms, alkoxy having from 1 to 4 carbon atoms, hydroxyl, phenyl or substituted phenyl; or
X is oxygen or sulfur if
$R^4$ is an $-NH_2$, $-NH-C_{1-4}$-alkyl, $-NH-C_{3-6}$-cycloalkyl, $-NH$-phenyl or $-NH-C_{1-4}$-alkyl-phenyl group; and
$R^5$ and $R^6$ independently stand for hydrogen, alkyl having from 1 to 4 carbon atoms or phenyl, with the proviso that at least one of them is other than phenyl,
and salts thereof. If there is a double bond in the 1,2-position, the N-substitution yields quaternary compounds.

According to another aspect of the invention there is provided a process for the preparation of isoquinoline derivatives of the formula (I) and salts thereof.

Those compounds of the formula (I), in which
$R^3$ is alkyl having from 1 to 6 carbon atoms or aralkyl containing from 1 to 4 carbon atoms in the alkyl moiety,
$R^1$, $R^2$ and the dotted line are as defined above,
and—if there is a double bond in the 1,2-position—the quaternary salts thereof, can be prepared by N-alkylating or N-aralkylating a bis(hydroxymethyl)-methyl-isoquinoline derivative of the formula (II)

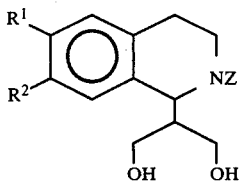
(II)

wherein
$R^1$, $R^2$ and the dotted line are as defined above, and
Z is hydrogen or a single electron pair,
and, if desired, hydrogenating a compound of the formula (I) obtained, having a double bond in the 1,2-position (process a/).

Compounds of the formula (I), in which $R^3$ is alkyl having from 1 to 6 carbon atoms, benzyl or a

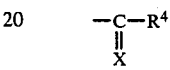

group, in which $R^4$ and X are as defined above, $R^1$ and $R^2$ have the same meanings as defined above, and there is a single bond in the 1,2-position, can be prepared by N-acylating a compound of the formula (IIA)

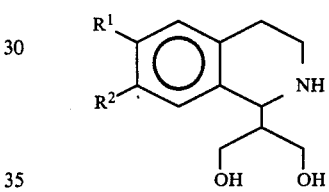
(IIA)

in which $R^1$ and $R^2$ are as defined above, with a suitable acid (thioacid) halide or anhydride, and, if desired, by reducing a compound of the formula (I), in which $R^3$ is a

group, and X is oxygen, $R^4$ is alkyl having from 1 to 5 carbon atoms or phenyl, obtained ($R^1$ and $R^2$ are is defined above) with a complex hydride, to yield a corresponding compound of the formula (I), in which $R^3$ is alkyl having from 1 to 6 carbon atoms or benzyl (process $b_1/$).

Compounds of the formula (I), in which $R^3$ is a

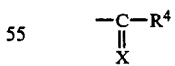

group, wherein
$R^4$ is $-NH_2$, $-NH-C_{1-4}$-alkyl, $-NH-C_{3-6}$-cycloalkyl, $-NH$-phenyl or $-NH-(C_{1-4}$-alkyl)-phenyl and
X is as defined above,
$R^1$ and $R^2$ are as defined above, and there is a single bond in the 1,2-position,
can be prepared by reacting a compound of the formula (IIA), in which $R^1$ and $R^2$ are as defined above, with an isocyanate or isothiocyanate of the formula (III)

R⁷NCX                                    (III)

wherein
X has the same meanings as defined above, and
R⁷ is alkyl having from 1 to 4 carbon atoms, cycloalkyl having from 3 to 6 carbon atoms, phenyl, alkylphenyl containing from 1 to 4 carbon atoms in the alkyl moiety or an alkali metal, (process b₂/).

Compounds of the formula (I), in which
R³ is a

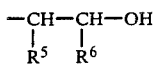

group,
R⁵, R⁶ as well as R¹ and R² are as defined above,
can be prepared by reacting a compound of the formula (IIA), wherein R¹ and R² are as defined above, with the epoxides of the formula (IV)

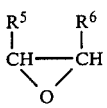                     (IV)

or halohydrines of the formula (V),

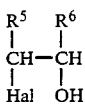                     (V)

wherein R⁵ and R⁶ are as defined above and Hal is halogen (process b₃/).

If desired, in the compounds of the formula (I) R¹ and/or R² and/or R³ can be converted into another group within the definition of R¹, R² and R³, respectively, in a manner known per se. If desired, compounds of the formula (I) can be converted into the acid addition salts thereof.

The compounds of the formula (I) are biologically active, e.g. possess valuable analgesic, antipyretic, immunsuppressive or anticonvulsive activity. Moreover, compounds of the formula (I) are valuable intermediates in the preparation of other, biologically active isoquinoline derivatives, which are e.g. disclosed in our co-pending Hungarian patent application No. 3653/83 which corresponds to U.S. application Ser. No. 664,849 filed Oct. 25, 1984. The latter compounds can be prepared by transforming the hydroxyl(s) of the bis(hydroxymethyl)-methylene group in the compounds of the formula (I) into other substituents in a conventional manner.

According to Chem. Ber. 102, 915 /1969/ 1-[bis(hydroxymethyl)-methyl]-isoquinoline was prepared from 1-methyl-isoquinoline with formaldehyde. The compound was afforded in a yield of 60%, after boiling for 40 hours. The only reaction of the compound obtained examined in the cited article was its hydrogenation in the presence of a platinum oxide catalyst, which resulted in the corresponding 5,6,7,8-tetrahydro-isoquinoline in a 30% yield. No N-substituted derivatives of these compounds were prepared, and it was neither disclosed nor suggested that these compounds or their derivatives would be pharmaceutically active.

In the above formulae, in the definition of R¹, R² and R⁴ the term "alkoxy" is used to refer to straight or branched chained alkoxy groups, e.g. methoxy, ethoxy, n- or isopropoxy, n-, sec.- or tert.-butoxy, n- or isopentoxy, n- or isohexyloxy groups, depending on the limitation given for the number of carbon atoms. The preferred alkoxy groups contain 1 to 4 carbon atoms, more preferably they are methoxy or ethoxy.

The term "alkyl" as such or as part of other groups is used to refer to straight-chained or branched alkyl groups, such as e.g. methyl, ethyl, n-propyl, isopropyl, n-butyl, isobutyl, sec.-butyl, tert.-butyl, n-pentyl, isopentyl, n-hexyl and isohexyl groups, taking into account the limitations for the number of carbon atoms.

The term "aralkyl containing from 1 to 4 carbon atoms in the alkyl moiety" in the definition of R³ preferably represents a C₁₋₄-alkyl-phenyl group, more preferably benzyl.

In the definition of R⁴ "phenyl" may be substituted by one or more substituents, preferably selected from the group consisting of halogen, alkyl having from 1 to 4 carbon atoms, alkoxy having from 1 to 4 carbon atoms and nitro. The term "halogen" is used to include all halogen atoms, i.e. fluorine, chlorine, bromine and iodine, preferably chlorine.

As a cycloalkyl in the definition of R⁴ preferably cyclohexyl is used.

The starting compounds of the formulae (II) and (IIA) are disclosed in our co-pending Hungarian Patent Application No. 3651/83 which corresponds to U.S. application Ser. No. 664,842 filed Oct. 25, 1984, and can be prepared by reacting the corresponding 1-methyl-3,4-dihydroisoquinoline derivatives or 1-(β-hydroxyethyl)-3,4-dihydroisoquinoline derivatives with formaldehyde, the hydrate or trimeric derivative thereof, preferably in an alkaline medium. The 1,2,3,4-tetrahydro-derivatives [formula (IIA)] are prepared by hydrogenation of the respective 3,4-dihydro-compounds.

The N-alkylation or N-aralkylation of the starting compounds of the formula (II) (R¹, R² and the dotted line are as defined above, and Z is hydrogen or a single electron pair) in process a/ can be carried out by any conventional technique known in the art. It may, for example, be performed with alkyl or aralkyl halides, preferably chlorides, bromides or iodides, preferably in an organic solvent inert under the reaction conditions, more preferably in an aliphatic alkanol, e.g. absolute ethanol; ketone, e.g. acetone or butylethyl ketone; or acetonitrile, in the presence of an acid binding agent, e.g. alkali metal hydroxide, carbonate or alcoholate or an organic base, such as e.g. quaternary ammonium compounds. This reaction is preferably accomplished at elevated temperature, though the temperature is not critical as to the result of the reaction.

The N-methyl derivatives may be prepared also with an aqueous formaldehyde solution in the presence of anhydrous formic acid, at elevated temperature.

Quaternization of the compounds containing a double bond in the 1,2-position is preferably carried out with alkyl or aryl halides, preferably bromides or iodides, in an inert organic solvent, e.g anhydrous aliphatic alkanols having from 1 to 6 carbon atoms, e.g. absolute ethanol; ketones, e.g. acetone or methylethyl ketone; or acetonitrile, at elevated temperature.

In process b₁/ the acylation of the starting compounds of formula (IIA)—wherein R¹ and R² are as defined above—may be carried out by conventional N-acylation techniques known in the art. As an acylation agent carboxylic acid halides or anhydrides are generally employed.

When carboxlic acid halides are used for the acylation, the reaction is preferably carried out in an inert solvent, preferably benzene, in the presence of an acid binding agent, e.g. sodium hydroxide, at room temperature. The acylation with carboxylic acid anhydrides is generally carried out in the presence of an inert solvent or without any solvent, at room temperature or at elevated temperature.

The compounds of the formula (I), in which $R^3$ represents a

group, wherein X is oxygen, $R^4$ stands for an alkyl group having from 1 to 5 carbon atoms or phenyl, may be converted into the corresponding compounds of the formula (I), containing an alkyl having from 1 to 6 carbon atoms or benzyl as $R^3$, by reduction with a complex metal hydride. As a complex metal hydride for example lithium-aluminium hydride or sodium borohydride may be employed. The reaction is performed in an inert organic solvent, at elevated temperature, preferably at about the boiling point of the reaction mixture.

According to process b$_2$/ compounds of the formula (IIA)—wherein $R^1$ and $R^2$ are as hereinbefore defined—are reacted with the isocyanates or isothiocyanates of the formula (III)—wherein X and $R^7$ have the same meanings as hereinbefore defined—in an inert solvent, preferably at elevated temperature. As a solvent preferably an apolar, inert organic solvent, such as benzene is employed. The reaction is preferably carried out under reflux.

According to process b$_3$/ compounds of the formula (I), in which $R^3$ represents a

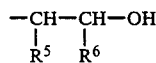

group—wherein $R^5$ and $R^6$ have the same meanings as defined above—are prepared by reacting compounds of the formula (IIA), wherein $R^1$ and $R^2$ are as defined above, with the epoxides of the formula (IV) or halohydrines of the formula (V), in which $R^5$, $R^6$ and Hal are as hereinbefore defined. The reaction is generally carried out in an inert organic solvent, such as an aliphatic alkanol having from 1 to 6 carbon atoms, preferably ethanol. The reaction temperature may be varied within wide limits but the reaction is preferably performed at room temperature or a slightly elevated temperature.

As mentioned before, in the compounds of the formula (I) the substituents $R^1$ and/or $R^2$ and/or $R^3$ can easily be converted into other substituents within the definition of $R^1$, $R^2$ and $R^3$, respectively. For example compounds of the formula (I), in which $R^1$ and/or $R^2$ is hydroxy, can be converted into the corresponding compounds of the formula (I), in which $R^1$ and/or $R^2$ represent an alkoxy group having from 1 to 6 carbon atoms, by methods known in the art. The 6,7-dimethoxy compounds are most expediently prepared by methylation of the corresponding 6,7-dihydroxy-compounds with diazomethane or dimethyl sulfate. The higher ethers can for example be prepared by the Williamson synthesis, using alkyl iodides. On the other hand, from compounds of the formula (I), in which R and/or $R^2$ represent an alkoxy group having from 1 to 6 carbon atoms, the corresponding compounds containing hydroxyl as $R^1$ and $R^2$ can be obtained by known reactions, e.g. heating with hydrogen iodide or by means of anhydrous aluminium chloride. Similarly, an $R^3$ acyl group can be converted into a corresponding alkyl or aralkyl group, depending on the meanings of $R^4$.

Compounds of the formula (I) can be converted into their acid addition salts by reaction with suitable acids. Salt formation can be carried out, for example, in an inert organic solvent such as a $C_{1-6}$ aliphatic alcohol, by dissolving the compound of the formula (I) in the solvent and adding the selected acid or a solution thereof formed with the same solvent to the first solution until it becomes slightly acidic (pH 5 to 6). Thereafter the acid addition salt separates and may be removed from the reaction mixture e.g. by filtration.

The compounds of the formula (I) or the salts thereof, if desired, can be subjected to further purification, e.g. recrystallization. The solvents used for recrystallization are selected depending on the solubility and crystallization properties of the compound to be crystallized.

The new compounds of the formula (I) and their physiologically acceptable salts may be formulated for therapeutical purposes. The invention therefore relates also the pharmaceutical compositions comprising, as active ingredient, at least one compound of formula (I) or a physiologically acceptable salt thereof, in association with a pharmaceutical carrier or excipient. Carriers conventional for this purpose and suitable for parenteral or enteral administration as well as other additives may be used. As carriers solid or liquid compounds, for example water, gelatine, lactose, milk sugar, starch, pectin, magnesium stearate, stearic acid, talc, vegetable oils, such as peanut oil, olive oil, arabic gum, polyalkylene glycols, Vaseline (registered trade-mark) can be used. The compounds can be formulated as conventional pharmaceutical formulations, for example in a solid (globular and angular pills, dragées, capsules, e.g. hard gelatine capsules, suppositories, etc.) or liquid (oily or aqueous solutions, suspensions, emulsions, syrups, soft gelatine capsules, injectable oily or aqueous solutions or suspensions) form. The quantity of the solid carrier can be varied within wide ranges, but preferably is between 25 mg and 1 g. The compositions optionally contain also conventional pharmaceutical additives, such as preserving agents, wetting agents, salts for adjusting the osmotic pressure, buffers, flavouring and aroma materials. The compositions according to the invention optionally contain the compounds of the formula (I) in association with other, known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For the pharmacological tests CFLP (LATI) mice of both sexes, weighing 18 to 22 g each and male Han. Wistar (LATI) rats weighing 160 to 180 g each were used. The test materials were administered orally, in 30 mg/kg doses, in the form of a suspension containing 5% of Tween 80, one hour before the tests.

TEST METHODS

1. Maximum Electroshock (mice)

The shock was applied through a corneal electrode (20 mA, 0.2 msec, HSE Schockgerät typ. 207). The animals which do not show a tonic, extensoric spasm as a result of electroshock treatment are considered protected (see Swinyard et al.: J. Pharmacol. Exp. Ther. 106, 319 /1952/).

2. Metrazole Spasm (mice)

After pretreatment, the animals were administered 125 mg/kg of pentylenetetrazole subcutaneously. The animals, which did not show a) a clonic, b) a tonic extensoric spasm and which survived the experiment, were regarded protected.

Observation time: one hour (Everett L. M. and Richards R. K.: J. Pharmacol. Exp. Ther. 81, 402 /1944/).

3. Inhibition of Tetrabenazine Catalepsy

The test was carried out on male rats each weighing 160 to 180 g. The test materials were administered intraperitoneally, in a dose of 30 mg/kg, one hour before tetrabenazine administration. The animals which, if their forlegs were placed on a 7 cm high pillar, did not correct their bizarre position within 30 seconds were regarded cataleptic (Delay J. and Denicker P.: Compt. Rend. Congr. Med. Alenistens Neurologists 19, 497 /Luxemb./).

4. Analgesic Activity (mice)

One hour after pretreatment, mice were administered 0.4 ml of a 0.6% acetic acid solution intraperitoneally, as a pain stimulus. The frequency of writhing syndrom is registered for 30 minutes. The changes observed as a result of treatment with the test compounds is related to the mean value of the frequency of writhing syndrom in the control group, and the difference is expressed in percentage (Koster R. et al.: Exp. Ther. 72:74 /1941/).

5. Antipyretic Activity (rats)

Hyperthermia is induced in rats with Brewer's yeast suspension (0.5% of Brewer's yeast, 1% of arabic gum in a volume of 0.3 ml, s.c.). The animals are treated with the test materials 4 hours later, and the tracheal temperature of the animals is registered with an ELAB thermometer (typ. TE-3) for 4 hours. The antipyretic activity is expressed in percentage of the animals which have at least one centigrade lower temperature than the average of the control group treated with the solvent (Nimegeers C. J. E. et al.: Arzneimittel Forsch. 25:15/9 /1975/).

It has been found that 1-[bis(hydroxmethyl)-methyl]-2-methyl-6,7-dimethoxy-1,2,3,4-tetrahydro-isoquininoline hydrochloride (compound A) has valuable analgesic activity. This compound is four times more active than the reference compound (Na-salicylate) and its main activity is accompanied with remarkable anticonvulsive and antidepressive effects. 1-[bis-(Hydroxymethyl)-methyl]-2-(β-hydroxybutyl)6,7-diethoxy-1,2,3,4-tetrahydroisoquinoline hydrochloride (compound B) has a somewhat lower analgesic activity than the above 2-methyl-compound, but the writhing syndrom induced with acetic acid is practically not influenced by a 30 mg/kg dose of the reference compound. The results are set forth in Table 1 below.

TABLE 1

| Materials | Antispasm activity max. electroshock | Antispasm activity metrazole a | Antispasm activity metrazole b | Antitetra-benazine activity (%) | Analgesic activity (%) | Antipyretic activity (%) |
| --- | --- | --- | --- | --- | --- | --- |
| Compound A | — | — | 20.0 | 20.0 | 28.0$^x$ | 20.0 |
| Compound B | — | — | 20.0$^x$ | 20.0 | 40.0 | 20.0 |
| Na—salicylate | — | — | 20.0 | — | 113.0$^x$ | 40.0 |

— = ineffective
20$^x$ = ED$_{50}$ (mg/kg)

The invention is elucidated in detail by the aid of the following non-limiting examples.

EXAMPLE 1

Preparation of 1-[bis(hydroxymethyl)-methyl]-2-methyl-6,7-dimethoxy-3,4-dihydroisoquinolinium iodide 0.03 mole (7.96 g) of 1-[bis(hydroxymethyl)-methyl]-6,7-dimethoxy-3,4-dihydroisoquinoline is dissolved in 40 ml of absolute ethanol. 0.045 mole (6.39 g) of methyl iodide is added to the solution and the reaction mixture is kept at 30° to 40° C. for 6 hours. The precipitated crystals are filtered off and recrystallized from ethanol. The aimed compound is obtained with a melting point of 189° to 193° C.

Yield: 71%.

Analysis for C$_{15}$H$_{22}$INO$_4$ (407.26): calculated: C 44.24%, H 5.45%, N 3.44%; found: C 44.78%, H 5.62%, N 3.31%.

EXAMPLE 2

Preparation of 1-[bis(hydroxymethyl)-methyl]-2-benzyl-6,7-dimethoxy-3,4-dihydroisoquinolinium bromide 0.015 mole (4 g) of 1-[bis(hydroxymethyl)-methyl]-6,7-dimethoxy-3,4-dihydroisoquinoline is dissolved in 40 ml of absolute ethanol. 0.02 mole (3.4 g) of benzyl bromide is added to the solution and the reaction mixture is refluxed for 4 hours, under stirring. After cooling the crystals separated out are filtered off and recrystallized from ethanol. The aimed compound is obtained with a melting point of 178° to 179° C.

Yield: 59%.

Analysis for C$_{21}$H$_{26}$BrNO$_4$: calculated: C 57.80%, H 6.01%, N 3.21%; found: C 57.53%, H 7.88 %, N 3.33%.

EXAMPLE 3

Preparation of 1-[bis(hydroxymethyl)-methyl]-2-methyl-6,7-dimethoxy-1,2,3,4-tetrahydroisoquinoline hydrochloride To 0.0125 mole (3.33 g) of 1-[bis(hydroxymethyl)-methyl]-6,7-dimethoxy-1,2,3,4-tetrahydroisoquinoline 15 ml of a 37% aqueous formaldehyde solution and 15 ml of 99% formic acid are added. The reaction mixture is then kept at 100° C. for 10 hours. After cooling 50 ml of a 15% aqueous hydrochloric acid solution are added to the reaction mixture, which is then evaporated under reduced pressure. After thoroughly dehydrating the reaction mixture it is triturated with a small amount of acetone to yield the aimed compound with a melting point of 199° to 201° C. (ethanol/ether).

Yield: 50%.

Analysis for $C_{15}H_{26}ClNO_4$ (317.81%): calculated- C 56.68%, H 7.61%, N 4.41%; found: C 56.48%, H 7.43%, N 4.23%.

EXAMPLE 4

Preparation of 1-[bis(hydroxymethyl)-methyl]-2-benzoyl-6,7-dimethoxy-1,2,3,4-tetrahydroisoquinoline 0.01 mole (2.7 g) of 1-[bis(hydroxymethyl)-methyl]-6,7-dimethoxy-1,2,3,4-tetrahydroisoquinoline is dissolved in 50 ml of benzene under slight warming, and the solution obtained is admixed with a solution of 0.015 mole (0.6 g) of sodium hydroxide in 10 ml of water. 0.011 mole (1.5 g) of benzoyl chloride is added dropwise to the reaction mixture under cooling and stirring. When the addition is complete, the reaction mixture is stirred at room temperature for an additional hour, the organic phase is separated, and the aqueous phase is extracted twice with chloroform. The organic phases are combined, dried and evaporated to yield the aimed compound with a melting point of 161° to 163° C. (methanol/ether).

Yield: 95%.

Analysis for $C_{21}H_{25}NO_5$ (371.43): calculated: C 67.91%, H 6.78%, N 3.77%; found: C 67.72%, H 6.98%, N 4.00%.

The compounds of the formula (I/1) listed in Table 1 can be prepared in an analogous manner.

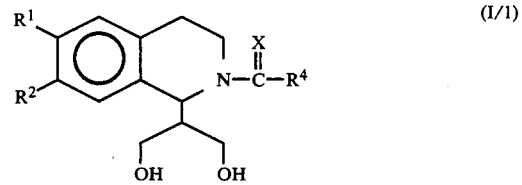

(I/1)

TABLE 1

| | | 1-[bis(Hydroxymethyl)-methyl]-2-acyl-6,7-dialkoxy-1,2,3,4-tetrahydroisoquinoline derivatives of formula (I/1) | | | | | | |
|---|---|---|---|---|---|---|---|---|
| Example | $R^1 = R^2$ | $R^4$ | Formula and mol. weight | X | Mp. [°C.] solvent | Analysis | calculated | found | Yield [%] |
| 5 | $CH_3O$ | $CH_3$ | $C_{16}H_{23}NO_5$ 309.35 | 0 | 129–131 EtOAc | C: H: N: | 62.12 7.48 4.53 | 62.05 7.57 4.72 | 84 |
| 6 | $C_2H_5O$ | $CH_3$ | $C_{18}H_{27}NO_5$ 337.41 | 0 | 101–103 acetone/ ether | C: H: N: | 64.07 8.07 4.15 | 63.85 7.92 3.94 | 87 |
| 7 | $C_2H_5O$ | $C_6H_5$ | $C_{23}H_{29}NO_5$ 399.49 | 0 | 145–147 acetone | C: H: N: | 69.15 7.32 3.51 | 68.69 7.81 4.07 | 87 |
| 8 | $CH_3O$ | $C_6H_4CH_3(p)$ | $C_{22}H_{27}NO_5$ 385.45 | 0 | 175–180 ethyl- acetate | C: H: N: | 68.55 7.06 3.63 | 68.39 7.31 3.25 | 85 |
| 9 | $C_2H_5O$ | $C_6H_4CH_3(p)$ | $C_{24}H_{31}NO_5$ 413.52 | 0 | 145–148 ethanol | C: H: N: | 69.71 7.56 3.39 | 70.04 7.54 3.32 | 83 |
| 10 | $CH_3O$ | $C_6H_4Cl(p)$ | $C_{21}H_{24}ClNO_5$ 405.88 | 0 | 173–176 acetone/ ether | C: H: N: | 62.14 5.96 3.45 | 61.91 6.21 3.00 | 95 — |
| 11 | $C_2H_5O$ | $C_6H_4Cl(p)$ | $C_{23}H_{28}ClNO_5$ 433.94 | 0 | 129–131 ethanol | C: H: N: | 63.66 6.50 3.32 | 63.58 6.96 3.32 | 90 |
| 12 | $C_2H_5O$ | $C_6H_4NO_2(p)$ | $C_{23}H_{28}N_2O_7$ 444.49 | 0 | 155–157 benzene | C: H: N: | 62.15 6.35 6.30 | 62.07 6.62 6.23 | 85 |
| 13 | $CH_3O$ | $C_6H_3(OCH_3)_2(\underline{m}.p)$ | $C_{23}H_{29}NO_7$ 431.47 | 0 | 166–169 ethanol | C: H: N: | 64.02 6.77 3.25 | 64.39 6.45 3.38 | 93 |
| 14 | $C_2H_5O$ | $C_6H_3(OCH_3)_2(\underline{m}.p)$ | $C_{25}H_{33}NO_7$ 459.52 | 0 | 135–137 ethanol | C: H: N: | 65.34 7.24 3.05 | 65.57 7.49 2.93 | 89 |
| 15 | $C_2H_5O$ | $C_6H_2(OCH_3)_3(\underline{m}.p.\underline{m}.)$ | $C_{26}H_{35}NO_8$ 489.57 | 0 | 179–181 acetone | C: H: N: | 63.79 7.21 2.86 | 63.31 7.02 2.32 | 98 |
| 16 | $CH_3O$ | $C_6H_3Cl_2(\underline{m}.p.)$ | $C_{21}H_{23}Cl_2NO_5$ 440.31 | 0 | 164–168 ethanol | C: H: N: | 57.20 5.25 3.18 | 56.98 5.03 3.34 | 93 |
| 17 | $C_2H_5O$ | $C_6H_3Cl_2(\underline{m}.p)$ | $C_{23}H_{27}Cl_2NO_5$ 468.36 | 0 | 144–146 ethanol/ ether | C: H: N: | 58.98 5.81 2.99 | 59.13 5.97 2,78 | 82 |

EXAMPLE 18

Preparation of 1-[bis(hydroxymethyl)-methyl]-2-benzyl-6,7-dimethoxy-1,2,3,4-tetrahydroisoquinoline hydrochloride 0.01 mole (3.7 g) of 1-[bis(hydroxymethyl)-methyl]-2-benzoyl-6,7-dimethoxy-1,2,3,4-tetrahydroisoquinoline prepared according to Example 4 in 200 ml of absolute tetrahydrofuran is reacted with 4 g of lithium tetrahydroaluminate (III). The reaction mixture is refluxed for 3 hours, then it is worked up in a conventional manner and the corresponding hydrochloride is prepared in a manner known per se. The aimed compound is obtained with a melting point of 177° to 179° C. (ethanol/ether).

Yield: 69%.

Analysis for $C_{21}H_{28}ClNO_4$ (393.90): calculated: C 64.03%, H 7.16%, N 3.56%; found: C 63.65%, H 7.53%, N 3.12%.

1-[bis(hydroxymethyl)-methyl]-2-ethyl-6,7-dimethoxy-1,2,3,4-tetrahydroisoquinoline hydrochloride can be prepared in an analogous manner.

Melting point: 184° to 187° C. (ethanol/ether).
Yield: 73%.

Analysis for $C_{16}H_{26}ClNO_4$ (331.84): calculated: C 57.81%, H 7.90%, N 4.22%; found: C 57.60%, H 7.72%, N 4.59%.

EXAMPLE 19

Preparation of 1-[bis(hydroxymethyl)-methyl]-2-(β-hydroxyethyl)-6,7-dimethoxy-1,2,3,4-tetrahydroisquinoline hydrochloride 0.01 mole (2.7 g) of 1-[bis(hydroxymethyl)-methyl]-6,7-dimethoxy-1,2,3,4-tetrahydroisoquinoline is dissolved in 50 ml of ethanol, whereupon 0.015 mole (0.66 g) of ethylene oxide is added to the reaction mixture. The mixture is allowed to stand at room temperature for 3 to 4 days and is then evaporated to dryness. The oily residue obtained is converted into the corresponding hydrochloride with ethanol containing dry hydrogen chloride gas. The aimed compound is obtained.

Melting point: 216° to 218° C. (methanol).
Yield: 78%.

Analysis for $C_{16}H_{26}ClNO_5$ (347.84):
calculated: C 55.24%, H 7.54%, N 4.03%; found: C 55.20%, H 8.00%, N 3.85%.

The compounds of the formula (I/2) listed in Table 2 may be prepared in an analogous manner.

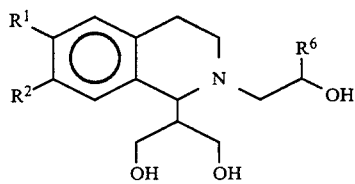

(I/2)

EXAMPLE 25

Preparation of 1-[bis(hydroxymethyl)-methyl]-2-carboethoxy-6,7-dimethoxy-1,2,3,4-tetrahydroisoquinoline To a solution of 0.01 mole (2.67 g) of 1-[bis-(hydroxymethyl)-methyl]-6,7-dimethoxy-1,2,3,4-tetrahydroisquinoline 0.01 mole (0.84 g) of sodium bicarbonate and 0.01 mole of chlorocarbonic acid ethyl ester are added. The mixture is boiled for one hour under stirring. After cooling the solution is extracted with ether. The extract is dried over sodium sulfate, evaporated to 10 to 20 ml and cooled. The aimed compound is obtained in a crystalline form.

Melting point: 103° to 105° C. (ethyl acetate).
Yield: 89%.

Analysis for $C_{17}H_{25}NO_6$ (339.38): calculated: C 60.16%, H 7.34%, N 4.13%; found: C 60.57%, H 7.02%, N 4.20%.

EXAMPLE 26

Preparation of 1-[bis(hydroxymethyl)-methyl]-2-[N'-phenylcarbamoyl]-6,7-dimethoxy-1,2,3,4-tetrahydroisoquinoline To a solution of 0.01 mole (2.7 g) of 1-[bis-(hydroxymethyl)-methyl]-6,7-dimethoxy-1,2,3,4-tetrahydroisoquinoline in 30 ml of absolute benzene 0.01 mole (0.3 g) of phenyl isocyanate is added, and the mixture is refluxed for 30 to 60 minutes. The reaction mixture is allowed to cool to room temperature, the precipitated crystals are filtered off, washed with ether and crystallized. The aimed compound is obtained with a melting point of 191° to 192° C. (ethyl acetate).
Yield: 91%.

Analysis for $C_{21}H_{26}N_2O_5$ (386.45): calculated: C 65.27%, H 6.78%, N 7.24%; found: C 65.39%, H 6.78%, N 7.52%.

The compounds of the formula (I/1) set forth in Table 3 can be prepared in an analogous manner. It should be noted that the reaction takes place quantitatively also at room temperature but the reaction time becomes considerably longer (2 to 3 days).

TABLE 2

1-[bis(Hydroxymethyl)-methyl]-2-(β-hydroxyalkyl)-6,7-dialkoxy-1,2,3,4-tetrahydroisoquinoline HCl derivatives of formula (I/2)

| Example | $R^1 = R^2$ | $R^6$ | Formula and mol. weight | Mp. [°C.] solvent | Analysis calculated | found | Yield [%] |
|---|---|---|---|---|---|---|---|
| 20 | $CH_3O$ | $CH_3$ | $C_{17}H_{28}ClNO_5$ 361.87 | 192–194 methanol | C: 56.43 H: 7.80 N: 3.87 | 56.08 8.16 3.64 | 92 |
| 21 | $C_2H_5O$ | $CH_3$ | $C_{19}H_{32}ClNO_5$ 389.92 | 144–147 acetone/ether | C: 58.53 H: 8.27 N: 3.59 | 58.51 8.06 3.27 | 85 |
| 22 | $CH_3O$ | $C_2H_5$ | $C_{18}H_{30}ClNO_5$ 375.90 | 203–205 acetone/ether | C: 57.52 H: 8.04 N: 3.73 | 58.04 7.91 4.10 | 95 |
| 23 | $C_2H_5O$ | $C_2H_5$ | $C_{20}H_{34}ClNO_5$ 403.95 | 131–134 ethanol/ether | C: 59.47 H: 8.48 N: 3.47 | 59.56 8.58 3.70 | 90 |
| 24 | $CH_3O$ | $C_6H_5$ | $C_{22}H_{30}ClNO_5$ 423.94 | 198–201 acetone/ether | C: 62.33 H: 7.13 N: 3.30 | 62.54 7.04 3.59 | 80 |

TABLE 3

Compounds of formula (I/1)

| Example | $R^1 = R^2$ | $R^4$ | Formula and mol. weight | X | Mp. [°C.] solvent | Analysis calculated | found | Yield [%] |
|---|---|---|---|---|---|---|---|---|
| 27 | $CH_3O$ | $NH-C_2H_5$ | $C_{17}H_{26}N_2O_4S$ | S | 134–135 | C: 57.59 | 57.98 | 87 |

TABLE 3-continued

| | | | Compounds of formula (I/1) | | | | | |
|---|---|---|---|---|---|---|---|---|
| Example | R¹ = R² | R⁴ | Formula and mol. weight | X | Mp. [°C.] solvent | Analysis calculated | found | Yield [%] |
| | | | 354.47 | | EtOAc | H: 7.39<br>N: 7.90 | 8.09<br>8.47 | |
| 28 | C₂H₅O | NH—C₂H₅ | C₁₉H₃₀N₂O₄S<br>382.52 | S | 118–120<br>ethanol/<br>ether | C: 59.65<br>H: 7.90<br>N: 7.32 | 58.27<br>8.27<br>7.37 | 88 |
| 29 | CH₃O | NH—C₆H₅ | C₂₁H₂₆N₂O₄S<br>402.51 | S | 158–160<br>EtOAc | C: 62.66<br>H: 6.51<br>N: 6.96 | 62.28<br>6.92<br>6.81 | 94 |
| 30 | C₂H₃O | NH—C₆H₅ | C₂₃H₃₀N₂O₄S<br>430.56 | S | 159–161<br>ethanol | C: 64.16<br>H: 7.02<br>N: 6.51 | 64.53<br>7.64<br>6.54 | 93 |
| 31 | CH₃O | NH—C₆H₁₁ | C₂₁H₃₂N₂O₅<br>392.49 | 0 | 183–185<br>EtOAc | C: 64.26<br>H: 8.26<br>N: 6.86 | 63.88<br>8.12<br>6.70 | 88 |
| 32 | CH₃O | NH—C₆H₁₁ | C₂₁H₃₂N₂O₄S<br>408.56 | S | 157–158<br>EtOAc | C: 61.74<br>H: 7.90<br>N: 6.86 | 61.36<br>8.11<br>6.70 | 86 |
| 33 | C₂H₅O | NH—C₆H₁₁ | C₂₃H₃₆N₂O₄S<br>436.61 | S | 148–150<br>benzene | C: 63.27<br>H: 8.31<br>N: 6.42 | 63.78<br>8.52<br>6.46 | 83 |

EXAMPLE 34

Preparation of 2-[bis(hydroxymethyl)-methyl]-2-methyl-6,7-dimethoxy-1,2,3,4-tetrahydroisoquinoline hydrochloride 0.01 mole (3.39 g) of 1-[bis(hydroxymethyl)-methyl]-2-(ethoxycarbonyl)-6,7-dimethoxy-1,2,3,4-tetrahydroisoquinoline is boiled with 3.5 g of lithium-tetrahydroaluminate(III) in absolute tetrahydrofurane for 3 hours. By working up the reaction mixture as described in the previous examples and treating the compound obtained with a 20% abs. ethanolic hydrogen chloride solution the aimed compound is obtained with a yield of 35%.

Melting point: 198° to 200° C. (ethanol/ether).

The spectral data of the product are identical with those of the compounds obtained in Example 3.

EXAMPLE 35

Preparation of 1-[bis(hydroxymethyl)-methyl]-6,7-dimethoxy-1,2,3,4-tetrahydroisoquinoline-N-thiocarboxamide 0.01 mole (2.67 g) of 1-[bis(hydroxymethyl)-methyl]-6,7-dimethoxy-1,2,3,4-tetrahydroisoquinoline is suspended in 10 ml of water, and to the suspension 0.012 mole (1.16 g) of potassium thiocyanate is added. The mixture is boiled for 6 hours. After cooling to room temperature the obtained substance is extracted with four 50-ml portions of ethyl acetate. The combined organic phases are dried and evaporated. Trituration of the obtained oily product yields the aimed compound in a crystalline form with a melting point of 146° to 148° C. (ethanol).

Yield: 39%.

We claim:

1. N-substituted bis(hydroxymethyl)-methylisoquinoline derivatives of the formula (I),

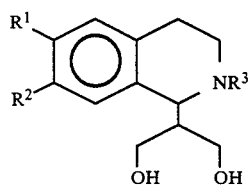

wherein
R¹ and R² represent hydroxyl or alkoxy having from 1 to 6 carbon atoms,
the dotted line is an optional double bond in the 1,2-position,
R³ is alkyl having from 1 to 6 carbon atoms or, phenyl-C₁-C₄-alkyl or—if there is a single bond in the 1,2-position—represents a group of the formula

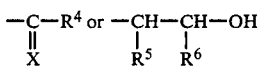

in which
X is oxygen if
R⁴ is alkyl having from 1 to 5 carbon atoms, alkoxy having from 1 to 4 carbon atoms, hydroxyl, phenyl or phenyl substituted by halogen, alkyl of 1-4 carbon atoms, alkoxy of 1-4 carbon atoms or nitro; or
X is oxygen or sulfur if
R⁴ is an —NH₂, —NH—C₁₋₄-alkyl, —NH—C₃₋₆-cycloalkyl, —NH-phenyl or —NHC₁₋₄-alkyl-phenyl group; and
R⁵ and R⁶ independently stand for hydrogen, alkyl having from 1 to 4 carbon atoms or phenyl, with the proviso that at least one of them is other than phenyl,
and physiologically acceptable salts thereof.

2. A compound of the formula I as defined in claim 1, wherein R³ is benzyl.

3. The compound of the formula I as defined in claim 1 which is 1-[bis(hydroxymethyl)-methyl]-2-methyl-6,7-dimethoxy-1,2,3,4-tetrahydroisoquinoline hydrochloride.

4. The compound of formula I as defined in claim 1 which is 1-[(bis-hydroxymethyl)methyl]-2-(β-hydroxybutyl)-6,7-diethoxy-1,2,3,4-tetrahydroisoquinoline hydrochloride.

5. A pharmaceutical composition having analgesic, antipyretic, immunsuppresive and anti-convulsive properties containing as active ingredient an effective amount of at least one compound of formula (I) as defined in claim 1 or a physiologically acceptable salt thereof, wherein R¹, R², R³ and the dotted line are as defined in claim 1, in association with a pharmaceutical carrier or excipient.

* * * * *